United States Patent
Hacke et al.

(10) Patent No.: US 8,342,179 B2
(45) Date of Patent: Jan. 1, 2013

(54) DISPOSABLE MASK ASSEMBLY WITH EXHAUST FILTER AND VALVE DISC AND METHOD OF ASSEMBLING SAME

(75) Inventors: Gerhard A. Hacke, Erin (CA); Cornel C. Hacke, Guelph (CA)

(73) Assignee: Respan Products, Inc., Erin, ON (CA)

( * ) Notice: Subject to any disclaimer, the term of this patent is extended or adjusted under 35 U.S.C. 154(b) by 924 days.

(21) Appl. No.: 12/385,487

(22) Filed: Apr. 9, 2009

(65) Prior Publication Data

US 2009/0250060 A1 Oct. 8, 2009

Related U.S. Application Data

(63) Continuation-in-part of application No. 11/269,678, filed on Nov. 9, 2005, now Pat. No. 7,559,323.

(51) Int. Cl.
*A62B 18/08* (2006.01)
(52) U.S. Cl. .......... 128/206.15; 128/206.12; 128/206.17
(58) Field of Classification Search ............ 128/206.12–206.17, 205.24–205.29; 137/512.15, 513.3, 137/513.5, 854
See application file for complete search history.

(56) References Cited

U.S. PATENT DOCUMENTS

| | | | |
|---|---|---|---|
| 2,139,137 A | 12/1938 | Schwartz | |
| 2,153,437 A | 4/1939 | Schwartz | |
| 2,505,173 A | 4/1950 | Conley | |
| 2,744,523 A | 5/1956 | Malcom et al. | |
| 2,744,524 A | 5/1956 | Whipple | |
| 2,744,525 A | 5/1956 | Whipple | |
| 2,843,121 A | 7/1958 | Hudson | |

(Continued)

OTHER PUBLICATIONS

Respan Products Inc., Respiratory Products Catalog—The Canadian Source for Respiratory Disposables, 2003, pp. 1-12, Erin, Ontario, Canada.

*Primary Examiner* — Loan Thanh
*Assistant Examiner* — Kathryn E Ditmer
(74) *Attorney, Agent, or Firm* — Roylance, Abrams, Berdo & Goodman, L.L.P.

(57) ABSTRACT

A face mask assembly and method of assembling a face mask is provided for a patient that includes a face piece sized to fit over the patient's nose and mouth. The face mask assembly forms a mask chamber between the face piece and the patient's nose and mouth. An inhalation adapter is coupled to the face piece to deliver medication to the chamber. A filter housing is coupled to the face piece and includes a flange section that defines a passageway to connect the mask chamber and the flange section. A filter is positioned in the filter housing. A cover is coupled to the flange section and has an exhalation opening or vent to allow gases from the mask chamber to pass through the filter and escape from the passageway to the atmosphere. In a second embodiment, the filter housing is modified by providing a frame adjacent the bottom with a cross-shaped structure and a retainer button attached to the housing. A valve disc is provided between the retainer button and frame adapted to allow gases from the mask chamber around the valve disc towards the filter. When a patient inhales oxygen through the nasal portion, the valve disc moves towards the mask and partially covers a plurality of apertures to partially block additional air from entering the chamber. When a patient exhales contaminated oxygen, the valve disc moves towards the retainer button to allow a maximum amount of air through the apertures towards the filter.

24 Claims, 5 Drawing Sheets

U.S. PATENT DOCUMENTS

| | | |
|---|---|---|
| 3,142,549 A | 7/1964 | Klusewitz et al. |
| 3,161,491 A | 12/1964 | Gongoll et al. |
| 3,266,490 A | 8/1966 | Klinger et al. |
| 3,527,242 A * | 9/1970 | Ansite ............................ 137/102 |
| D250,047 S | 10/1978 | Lewis et al. |
| 4,179,274 A | 12/1979 | Moon |
| 4,201,205 A | 5/1980 | Bartholomew |
| 4,207,882 A | 6/1980 | Lemere |
| 4,328,797 A | 5/1982 | Rollins et al. |
| 4,440,163 A | 4/1984 | Spergel |
| 4,588,631 A | 5/1986 | Clark |
| 4,630,604 A * | 12/1986 | Montesi ................... 128/206.15 |
| 4,649,912 A | 3/1987 | Collins |
| 4,657,010 A | 4/1987 | Wright |
| 4,846,166 A | 7/1989 | Willeke |
| 4,850,346 A | 7/1989 | Michel et al. |
| 4,934,361 A | 6/1990 | Michel et al. |
| 4,960,121 A | 10/1990 | Nelson et al. |
| 5,117,821 A | 6/1992 | White |
| 5,143,061 A | 9/1992 | Kaimer |
| 5,181,507 A | 1/1993 | Michel et al. |
| 5,222,488 A | 6/1993 | Forsgren |
| 5,226,412 A | 7/1993 | Winters |
| 5,240,479 A | 8/1993 | Bachinski |
| 5,374,458 A | 12/1994 | Burgio |
| 5,474,060 A | 12/1995 | Evans |
| 5,492,114 A | 2/1996 | Vroman |
| 5,505,197 A | 4/1996 | Scholey |
| 5,579,761 A | 12/1996 | Yuschak et al. |
| 5,647,356 A | 7/1997 | Osendorf et al. |
| 5,651,810 A | 7/1997 | Flaherty et al. |
| 5,758,642 A | 6/1998 | Choi |
| 5,776,213 A | 7/1998 | Flaherty et al. |
| 6,055,983 A | 5/2000 | Metzger |
| 6,176,237 B1 * | 1/2001 | Wunderlich et al. ...... 128/203.12 |
| 6,298,849 B1 | 10/2001 | Scholey et al. |
| 6,363,934 B2 | 4/2002 | Metzger |
| 6,412,514 B1 * | 7/2002 | Raftis ............................ 137/111 |
| 6,418,929 B1 | 7/2002 | Norfleet |
| 6,457,473 B1 | 10/2002 | Brostrom et al. |
| 6,497,232 B2 | 12/2002 | Fecteau et al. |
| 6,584,976 B2 | 7/2003 | Japuntich et al. |
| 6,659,102 B1 | 12/2003 | Sico |
| 6,701,925 B1 | 3/2004 | Resnick |
| 6,718,982 B2 | 4/2004 | Smith et al. |
| 6,732,733 B1 | 5/2004 | Brostrom et al. |
| 6,783,566 B2 | 8/2004 | Estkowski |
| 6,800,225 B1 | 10/2004 | Hagmann et al. |
| 6,854,464 B2 | 2/2005 | Mukaiyama et al. |
| 7,093,596 B2 | 8/2006 | Muller et al. |
| 7,114,496 B1 * | 10/2006 | Resnick et al. ........... 128/201.25 |
| 7,114,498 B1 | 10/2006 | Nashed |
| 2001/0035181 A1 | 11/2001 | Elkins |
| 2002/0078953 A1 | 6/2002 | Fecteau et al. |
| 2002/0162556 A1 | 11/2002 | Smith et al. |
| 2002/0189616 A1 | 12/2002 | Wolf |
| 2003/0127101 A1 | 7/2003 | Dennis |
| 2003/0154984 A1 | 8/2003 | Fernandes |
| 2004/0084048 A1 | 5/2004 | Stenzler et al. |
| 2005/0121029 A1 | 6/2005 | Reisman |
| 2007/0012360 A1 * | 1/2007 | Flynn ............................ 137/102 |
| 2007/0101990 A1 | 5/2007 | Hacke et al. |
| 2007/0295338 A1 * | 12/2007 | Loomas et al. ........... 128/207.18 |
| 2009/0260628 A1 * | 10/2009 | Flynn, Sr. ................ 128/203.28 |

* cited by examiner

DISPOSABLE MASK ASSEMBLY WITH EXHAUST FILTER AND VALVE DISC AND METHOD OF ASSEMBLING SAME

CROSS REFERENCE TO RELATED APPLICATION

This application is a continuation-in-part of and claims the benefit of U.S. patent application Ser. No. 11/269,678, filed Nov. 9, 2005 now U.S. Pat. No. 7,559,323, the subject matter of which application is hereby incorporated herein by reference in its entirety.

FIELD OF THE INVENTION

The present invention relates to a face mask assembly to filter a patient's exhalation and allow a minimum inhalation if necessary. More particularly, the present invention relates to a face mask assembly including a face piece having a filter positionable between a filter housing and a snap-fitting cover with an exhalation vent. The filter housing also is snap-fitted to the mask face piece. The filter housing includes a valve disc attached to the portion of the housing closest to the mask piece to prevent a large volume of external air from entering the mask when a patient inhales. The flexible discs are adjacent to the mask piece to permit air to be released from the mask when a patient exhales.

BACKGROUND OF THE INVENTION

Breathing masks configured to administer gases (e.g. aerosol or oxygen) to a patient have been available for many years. However, these prior art devices are not entirely acceptable for a variety of reasons.

For example, U.S. Pat. No. 6,659,102 to Sico, the entire disclosure of which is hereby incorporated herein by reference, discloses an oxygen mask filter system for preventing the transmission of disease. The mask has an inhalation valve and a plurality of vent apertures mounted on opposing sides of the mask. Filter members are removably mounted on each side of the mask. The filter members are mounted by a post member having a flanged end. Consequently, the filter system is comparatively complex and utilizes a multitude of moving parts. Moreover, the interchangeability of the mask with multiple filters is relatively limited.

Another mask assembly is described in U.S. Pat. No. 5,579,761 to Yuschak et al., the entire disclosure of which is also hereby incorporated herein by reference. This mask assembly includes a respirator having a face piece and a cartridge receiving structure located on the face piece. The mask assembly uses an inhalation filter. An exhalation filter is not positioned between a flange portion and a cover with an exhalation vent to reduce exposure of harmful agents to others that may be in the same room as the patient using the mask. Therefore, healthcare personnel administering treatments to patients are exposed to free airborne medication mist which potentially causes infectious diseases.

Yet another mask assembly includes a plurality of apertures on the face piece. A flexible valve disc covers the apertures to prevent any inhaled air from entering through the apertures. When a patient exhales, the air flows through the apertures, around the disc, and is airborne. Therefore, healthcare professionals and emergency personnel administering treatments to patients are exposed to airborne contaminated oxygen particles. In addition, should the nasal portion of the mask fail where the patient is inhaling pure oxygen, there is a chance of suffocation because the valve disc would block any air from passing from the environment through the apertures since the valve disc completely surrounds the apertures.

Accordingly, in order to address these disadvantages, there have been various additional attempts to provide mask assemblies to reduce the transfer of bacteria/viruses to or from an infected patient. Examples of mask assemblies are disclosed in U.S. Pat. No. 4,440,163 to Spergel; U.S. Pat. No. 4,934,361 to Michel et al.; U.S. Pat. No. 5,226,412 to Winters; U.S. Pat. No. 5,647,356 to Osendorf et al.; U.S. Pat. No. 6,298,849 to Scholey et al.; and U.S. Pat. No. 6,584,976 to Japuntich et al., and U.S. Patent Publication No. 2004/0084048 to Stenzler et al.; the disclosures of each are hereby incorporated herein by reference in their entirety. Although some of the features of those mask assemblies ease the disadvantages described above, a continuing need exists for an improved mask assembly which minimizes or eliminates release of patient exhaled gases and/or surplus medication into room air; is readily interchangeable with a number of different types of filters; is relatively simple to use, make, and assemble; and which simultaneously reduces the number of parts necessary for manufacture and assembly.

SUMMARY OF THE INVENTION

An object of the present invention is to solve at least the above problems and/or disadvantages and to provide at least the advantages described below.

Accordingly, an object of the present invention is to provide a filter and a method of assembling a filter that makes it relatively simple to install the filter between the filter housing and a cover.

Another object of the present invention is to provide a mask assembly which reduces the number of parts necessary for manufacture and assembly.

A further object of the present invention is to provide a mask assembly which is readily interchangeable with a number of different types of filters and is relatively simple to make, use, and assemble.

Still another object of the present invention is to provide a mask assembly for allowing a continuous supply of oxygen and an exhalation of contaminants that are trapped on a filter.

Yet another object of the present invention is to provide a mask assembly with both a sealing surface against which a flexible valve disc closes during inhalation and a crosspiece with openings for the valve disc to expand away from during exhalation.

The foregoing objects are attained by providing a face mask assembly for a patient including a face piece sized to fit over the patient's nose and mouth, and forming a mask chamber between the face piece and the patient's nose and mouth; an inhalation adapter coupled to the face piece to deliver a fluid to the chamber; at least one filter housing coupled to the face piece and including a flange section, and defining a passageway to connect the mask chamber to the flange section; at least one filter positioned in the at least one filter housing; and at least one cover coupled to the at least one flange section, and having an exhalation vent to allow gases from the mask chamber to pass through the filter and escape from the passageway to the atmosphere.

The foregoing objects are also attained by providing a face mask assembly for a patient including face piece sized to fit over the patient's nose and mouth, and forming a mask chamber between the face piece and the patient's nose and mouth; an inhalation adapter coupled to the face piece to deliver a fluid to the chamber; at least one filter housing coupled to the face piece including a flange section, and defining a passageway connecting the mask chamber to the flange section; at least one filter positioned in the at least one filter housing; at least one cover coupled to the at least one flange section and having an exhalation vent to allow gases from the mask chamber to pass through the filter and escape from the passageway to the atmosphere.

The foregoing objects are further attained by providing a modified filter housing for a face mask assembly for a patient including a face piece sized to fit over the patient's nose and mouth, and forming a mask chamber between said face piece and the patient's nose and mouth; an inhalation adapter coupled to said face piece to deliver a fluid to said chamber; at least one filter housing coupled to said face piece including a flange portion, and defining a passageway connecting said mask chamber to said flange portion; a retainer button adjacent said face piece coupled to said filter housing; and a flexible valve disc coupled to said retainer button adapted to allow gases from said mask chamber to pass through said filter housing and escape from said passageway to the atmosphere.

The foregoing objects are further attained by providing a method of assembling a mask assembly for a patient, comprising the steps of positioning a face piece over the patient's nose and mouth to form a mask chamber between the face piece and the patient's nose and mouth; coupling an inhalation adapter to the face piece to deliver fluid to the mask chamber; arranging at least one filter housing including a flange section, and defining a passageway connecting the mask chamber to the flange portion on the face piece; positioning at least one filter positioned on a top surface of the flange portion of the filter housing; and coupling at least one cover to the at least one flange portion having an exhalation vent to allow gases from the mask chamber to pass through the filter and escape from the passageway to the atmosphere.

The foregoing objects are further attained by providing a method of delivering air to a patient, including the steps of providing a mask assembly having at least one opening adjacent a patient's face; snapping a filter housing with a bottom into the opening; securing a valve disc to the bottom between a retainer button and a frame of the filter housing; and distributing oxygen to a patient through the mask assembly and allowing gases to pass into and out of the mask assembly around the valve disc.

Other objects, advantages, and salient features of the invention will become apparent to those skilled in the art from the following detailed description, which, taken in conjunction with the annexed drawings, discloses preferred embodiments of the invention.

BRIEF DESCRIPTION OF THE DRAWINGS

The above and other objects, and features, and advantages of certain embodiments of the present invention will become more apparent from the following description taken in conjunction with the accompanying drawings, which form a part of this application and in which:

FIG. 4 is an enlarged side elevational view of the filter by itself;

Throughout the drawings, the same drawing reference numerals will be understood to refer to the same elements, features, and structures.

DETAILED DESCRIPTION OF THE EXEMPLARY EMBODIMENT OF FIGS. 1-4

Figure 1:
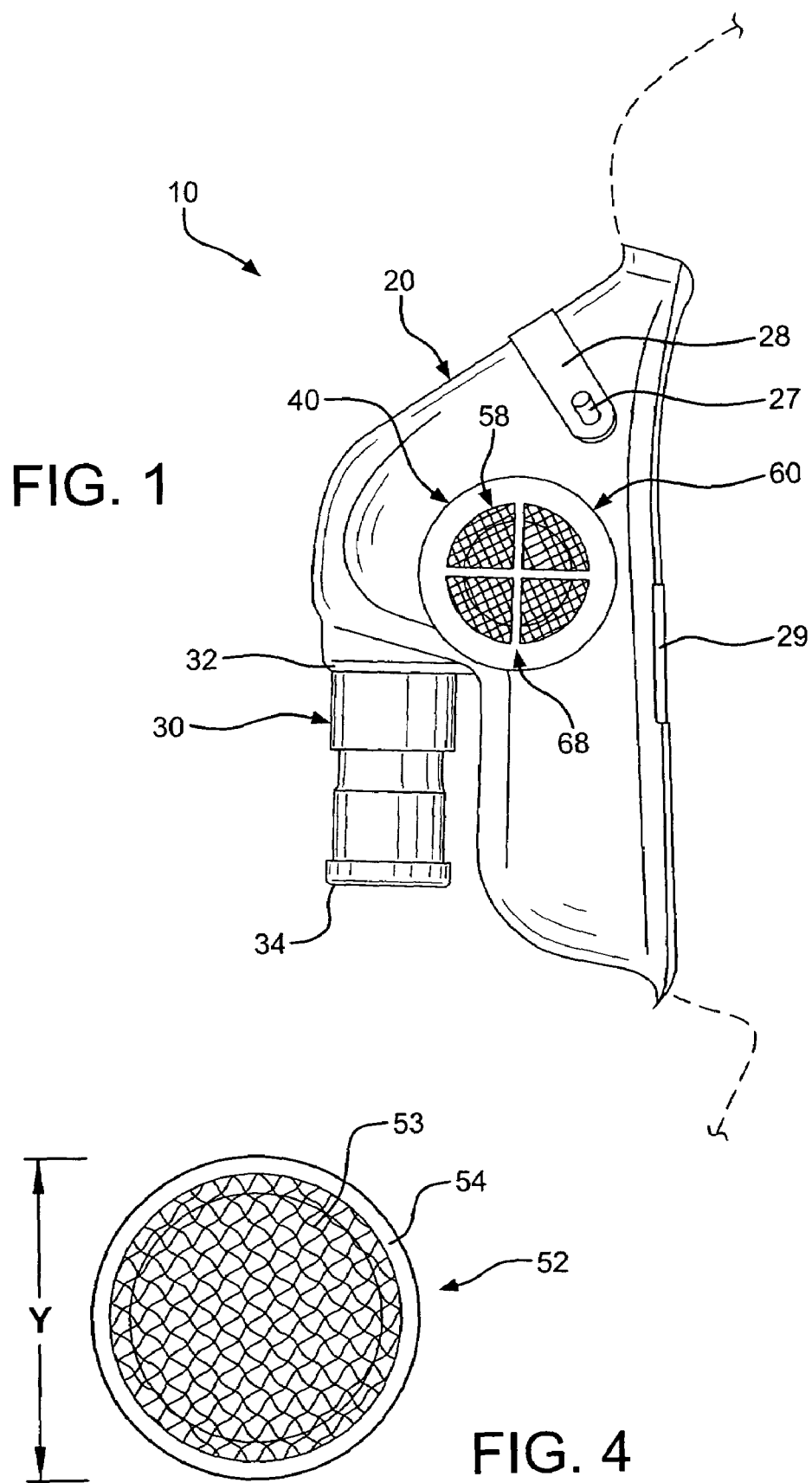
FIG. 1 is a side elevational view of a face mask assembly in accordance with an embodiment of the present invention.

Referring to FIGS. 1-4, a face mask assembly 10 in accordance with a first embodiment of the present invention is shown. The face mask assembly 10 includes a face piece 20 and an inhalation adapter 30. The mask assembly also includes a filter housing 40, a filter 52, and a cover 60 on each side.

Figure 2:
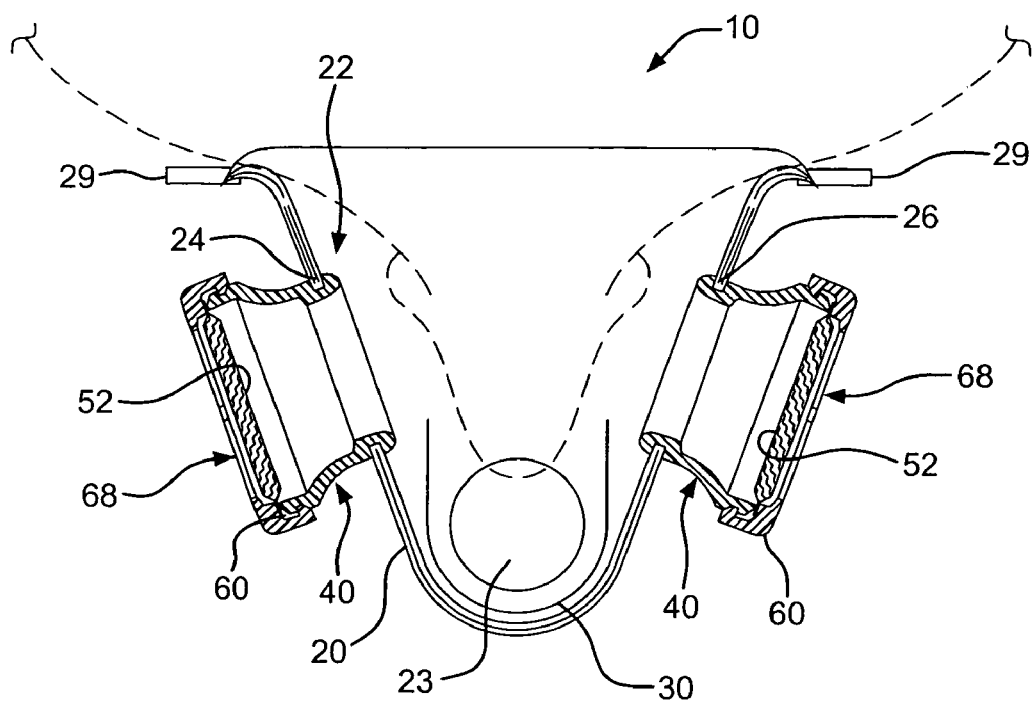
FIG. 2 is a top plan view in partial cross-section of the face mask assembly shown in FIG. 1.
Figure 3:
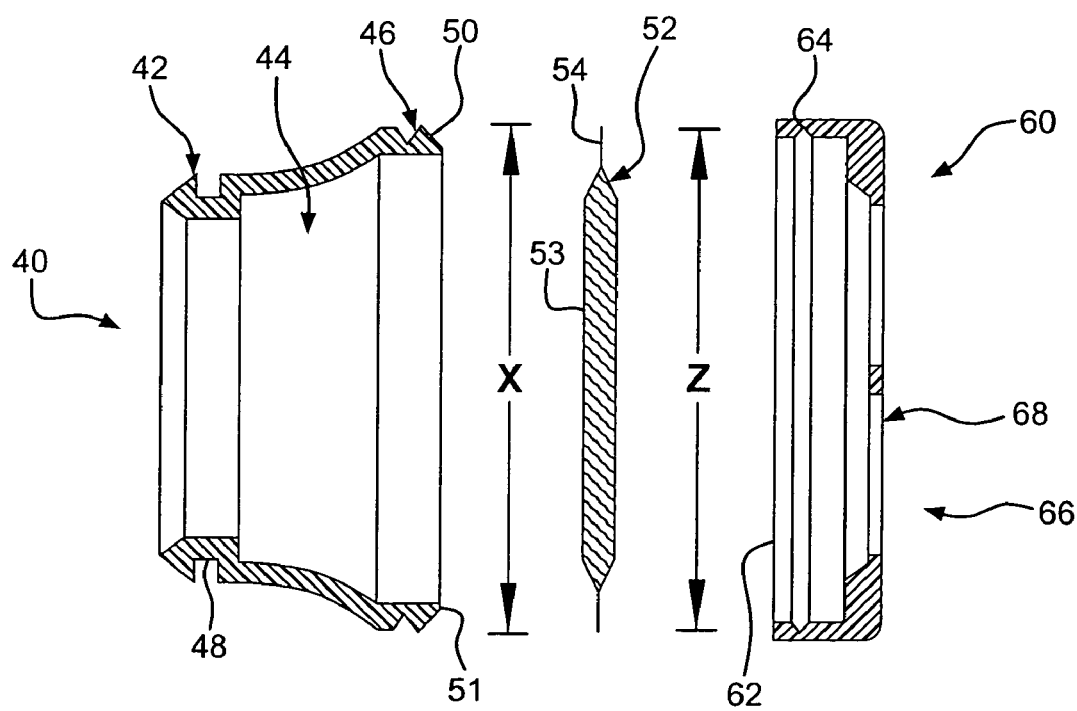
FIG. 3 is an enlarged and exploded top plan view in cross-section of a filter housing, filter, and cover of the face mask assembly shown in FIGS. 1-2.

As best seen in FIGS. 1-3, the face piece 20 preferably comprises a substantially curvilinear shaped shell configured to fit over the nose and mouth of a patient to establish a seal. As shown in FIG. 2, a breathing mask chamber 22 is formed between an inner surface of the face piece 20 and the nose and mouth of the patient. Preferably, a lower portion of the face piece is provided with an inhalation aperture 23. The inhalation aperture 23 enables a supply of air to travel into the mask chamber 22 from the inhalation adapter 30. Apertures 24 and 26 extend through the face piece 20 to receive a neck portion 42 (FIG. 3) of the two filter housings 40 via a snap fit. The apertures 24 and 26 fluidly connect the mask chamber 22 with a passageway 44 (FIG. 3) of the two filter housings 40. The apertures 24 and 26 preferably are substantially circular in shape; however, other suitable shapes and sizes may be used.

A portion of the face piece 20 is upturned. This upturned portion of the face piece is preferably substantially triangularly shaped to accommodate engagement with the bridge of a patient's nose as seen in FIGS. 1 and 2.

Turning to FIG. 1, one or more projections 27 are arranged on the outer surface of the face piece 20 proximate to the upturned portion. These projections 27 extend outwardly from the face piece and are configured to extend through apertures of a nose clip 28. The nose clip 28 enables the face piece 20 to adapt to a multitude of varying shaped nose bridges. Thus, a proper seal may be maintained within the mask chamber 22. As best seen in FIG. 1, the projections 27 are preferably upstanding, substantially cylindrical supports, and the apertures are preferably cylindrical; however, other suitable arrangements, sizes, and shapes may be used. The nose clip 28 is preferably a strip of resilient material such as aluminum.

At least two edges of the face piece 20 are provided with substantially polygonal shaped ears 29 (FIGS. 1 and 2). The ears 29 are preferably provided with apertures for receiving an engagement portion of a retaining strap (not shown); however, other suitable arrangements and constructions may be used. For example, alternatively, the retaining strap may have apertures and the ears 29 may have the engagement portion. The retaining strap is preferably made of a resilient material and adjustable. Thus, the length of the retaining strap may be adjusted for accommodating a multitude of patients' faces to establish a proper seal.

The face piece 20 is preferably constructed of a substantially light-weight, resilient, inert, and fire-resistant material such as, but not limited to, a rubber or plastic material. The face piece 20 is preferably relatively thin in cross-section so as to be soft and flexible. The face piece 20 is also preferably strong enough to resist the stress imposed thereon by the weight of the other components suspended therefrom.

As best seen in FIG. 1, the conventional inhalation adapter 30 has first and second open ends 32 and 34. The first end 32 of the inhalation adapter 30 is coupled to the face piece 20 via the inhalation aperture 23. The second end 34 of the inhalation adapter 30 may be configured to act as a plenum for a fluid supply source such as a pressurized gas bottle containing oxygen. The inhalation adapter 30 may also be used without pressurized gas. The inhalation adapter 30 may solely provide fluid such as aerosolized medication in combination with the oxygenated ambient atmosphere. Detailed descriptions of the inhalation adapter's 30 well-known conventional functions are omitted for clarity and conciseness. Accordingly, the inhalation adapter functions to sustain a breathable atmosphere within the mask chamber 22. The inhalation adapter 30 is preferably formed of a light-weight plastic. The inhalation adapter 30 is preferably coupled (e.g. bonded) to the face piece utilizing dichloromethane.

Turning to FIGS. 2-3, filter housing 40 will now be described. The filter housing 40 has inner and outer surfaces. The inner surface defines a fluid passageway 44. A first end of the filter housing 40 comprises a neck portion 42 and the second end of the filter housing 40 comprises a flange portion 46. The neck portion 44 defines a first opening. The flange portion 46 defines a second opening.

The neck portion 42 of the filter housing 40 includes a substantially annular groove 48 with a substantially U-shaped cross-section located in the outer surface of the filter housing 40. The filter housing 40 is preferably secured via a snap fit to the face piece 20 by forcing the neck portion 42 through the apertures 24 and 26 in the face piece 20 with a slight interference fit. Thus, groove 48 has a diameter slightly larger than the diameters of apertures 24 and 26, and engages the side edges of the apertures 24 and 26, thereby securing the filter housing 40 to the face piece 20. It is preferable that the width of the filter housing 40 increases from the neck portion 42 to the flange portion 46. Consequently, the width of the fluid passageway 44 gradually increases from the first end of the filter housing 40 to the second end.

The flange portion 46 has a substantially V-shaped annular projection 50 extending in a direction away from the outer surface of the filter housing 40 and has a diameter "x". It is preferable that the V-shaped projection 50 is configured to secure the cover 60 thereto via a snap fit. As stated above, since the outer surface of the filter housing 40 preferably expands outwardly from the neck portion 42, the flange portion 46 of the filter housing 44 has a predetermined width that is greater than the width of the neck portion 40 to accommodate engagement with the filter 52 on a top surface 51 thereof as described in further detail below and seen in FIGS. 1-4.

The filter housing 40 is preferably polypropylene injection molded and substantially cylindrical in shape. The filter housing 40 is preferably resilient and flexible to facilitate pushing of the neck portion 42 through the face piece 20 apertures 24 and 26. It should be understood that other suitable arrangements and constructions may be used.

The substantially disc-shaped filter 52 is best seen in FIG. 3. The middle portion 53 of the filter 52 has a substantially uniform cross-section. The filter 52 also has side edges, which gradually taper to a peripheral annular rim 54. A diameter "y" of the filter 52 rim 54 is about the same size as the diameter "x" of the flange portion 46 so that the filter 52 rim 54 engages the top surface 51 of the flange portion 46. The filter 52 is arranged so that it is positioned between the filter housing 40 and the cover 60 and simply secured thereto via engagement of the cover 60 on the housing 40 as described in further detail below and seen in FIGS. 1-4. Thus, fluid traveling through the fluid passageway 44 travels through the filter 52. Preferably a conventional electrostat filter 52 is utilized having permanent electrostatic charges to remove airborne particles. Such a filter 52 generally includes a uniform web of charged fibers to enable the media to capture particles throughout the depth of the filter 52 rather than only on the surface. The filter 52 is preferably for medical applications including anaesthetic gas/respiratory care, pulmonary function/spirometry and incubator filters. An example of such a filter 52 is the Ahlstrom Electrostat Filter Media HP150/410.

Turning to FIG. 3, the cover 60 is preferably substantially annular in shape. The cover 60 has an inner wall, an outer wall, a first end, and a second end. The first end defines a first opening 62 having a predetermined diameter. Disposed along the inner wall proximate the first opening is an annular groove 64 with a substantially V-shaped cross section having a maximum diameter "z" which is slightly smaller than diameter "x" of flange portion 46. This allows the cover 40 to snap fit over the flange portion 46 and stay secured thereto while keeping the filter rim 54 sandwiched and rigidly secured therebetween. The inner wall is substantially L-shaped. The inner wall extends upwardly from the first end, then inwardly, and then again upwardly to define the second opening or exhalation vent 66 in the second end. The second opening 66 also has a predetermined diameter that is preferably smaller than the width of the first opening 62. The second opening 66 is spanned by an X-shaped brace 68, which is integrally formed with cover 60 and helps to keep the filter 52 in place. The exhalation vent 68 has a plurality of openings. The type of fluid medium utilized determines the number and size of the openings for the brace 68.

The opening 66 acts as a vent to exhaust the gas contents within the mask chamber 22 to the ambient atmosphere. The filter 52 is positioned between the flange portion 46 of the filter housing 40 and the cover 60 having opening 66. Thus, the exhalation of toxic elements from the mask chamber 22 is minimized or eliminated and healthcare personnel are protected. Additionally, the rebreathing of medication aerosol deposited on filters may improve the medication delivery efficiency to the patient. The cover 60 is also preferable constructed of resilient polypropylene and injection molded.

Second Embodiment of FIGS. 5-13

In a second embodiment, illustrated in FIGS. 5-13, the filter housing 40 of the first embodiment is modified to accommodate a non-rebreather mask. More specifically, the bottom 100 of the filter housing 40 is modified with the addition of a valve disc 114 that partially restricts the flow of a gas into and out of the mask during inhalation and exhalation by the patient wearing the mask.

Figure 9:
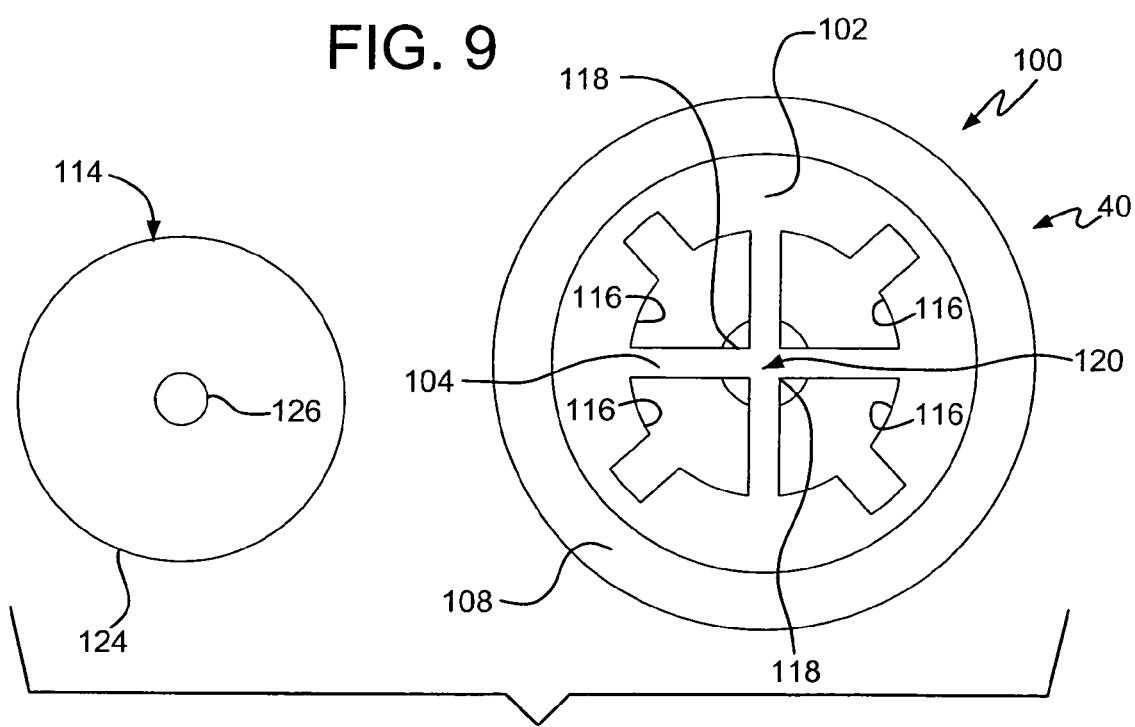
FIG. 9 is an enlarged, right side elevational view of the valve disc and the filter housing bottom shown in FIGS. 5-8 with the valve disc removed.

The filter bottom 100 includes a substantially planar frame 102 having a substantially cross-shaped surface 104 with a circular edge 106, surface 104 forming a valve seat for valve disc 114. A plurality of openings or apertures 116 are formed in the cross-shaped surface 104 and extend between the cross-shaped surface 104 from the circular edge 106, as seen in FIGS. 6-9. The apertures 116, as seen in FIG. 9, have an outer edge closest to the circular rim 102 and are arrowhead-shaped with the point 118 of the arrow facing the center 120 of the frame. The exterior side 108 of the filter bottom 100 further includes a recessed rim 109 for snap-fitting into the opening 110 of a mask assembly 10 as seen in FIG. 5.

Figure 5:
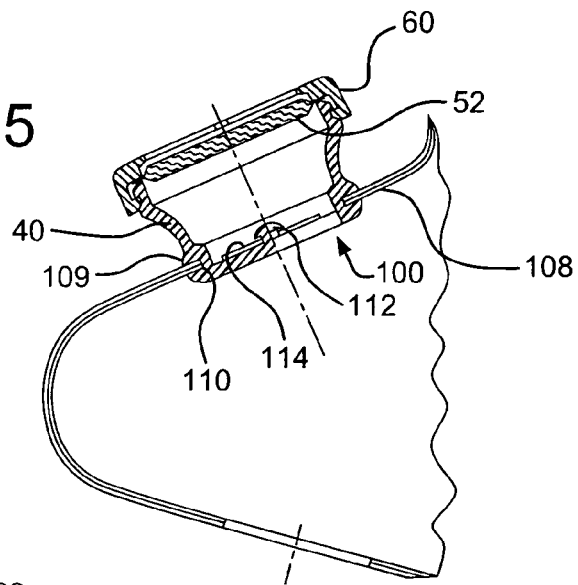
FIG. 5 is a top plan view in partial cross-section of the face mask assembly shown in FIGS. 1-3 with the modified filter housing in accordance with the second embodiment of the present invention.
Figure 6:
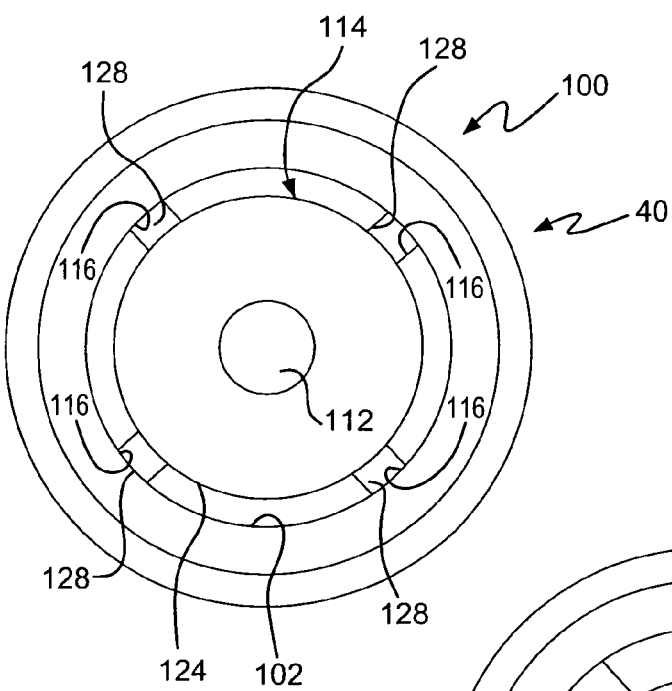
FIG. 6 is an enlarged, left side elevational view of the flexible valve disc coupled to the filter housing bottom shown in FIG. 5.
Figure 7:
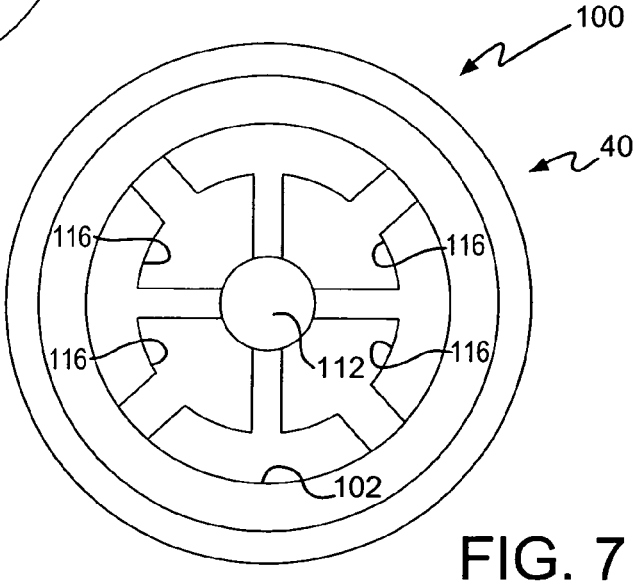
FIG. 7 is an enlarged, left side elevational view of the filter housing bottom shown in FIG. 6 but without the flexible valve disc located thereon.
Figure 8:
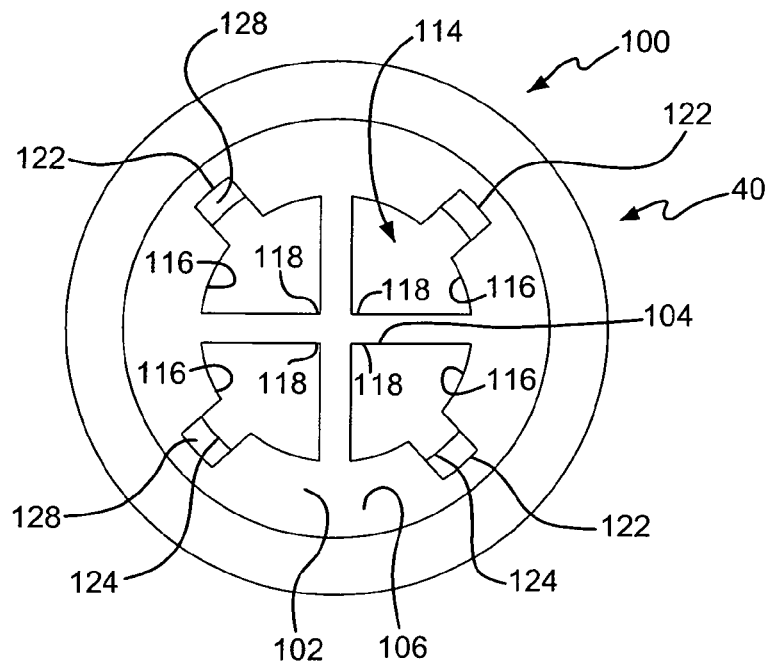
FIG. 8 is an enlarged, right side elevational view of the filter housing bottom shown in FIGS. 5 and 6 with the valve disc supported thereon.

As seen in FIG. 5, the filter bottom 100 is coupled to the face mask in a snap fit such that the bottom 100 is adjacent to the patient's face. The bottom 100 includes an outwardly-facing retainer button 112 on the interior side of the frame 102. A flexible valve disc 114 is disposed between the retainer button 112 and cross-shaped surface 104 of the frame 102. The diameter of the valve disc 114 is slightly smaller than that of the circular edge 106 and the outermost part of the four apertures 116.

As seen in FIG. 9, the valve disc 114 is substantially circular and made of a flexible and resilient material, such as rubber or polymeric material. The valve disc 114 has a circular opening 126 at its center. This allows the valve disc 114 to be placed around and snapped over retainer button 112, the opening 126 in the disc being smaller than the outer diameter of the button 112 but larger than the outer diameter of the cylindrical post 113 supporting button 112 and preferably being integrally formed with bottom 100 in the center thereof. The valve disc 114 is positioned between the retainer button 112 and frame 102. The space between the retainer button 112 and frame 102 is large enough to provide enough clearance for the valve disc 114 to move therebetween. As seen in FIGS. 5-13, the perimeter or exterior rim 124 of the valve disc 114 is disposed within the interior of and does not extend to the outermost portions 122 of the apertures 116 to form a permanent passageway or vent area 128 for a gas to pass therethrough.

Figure 11:
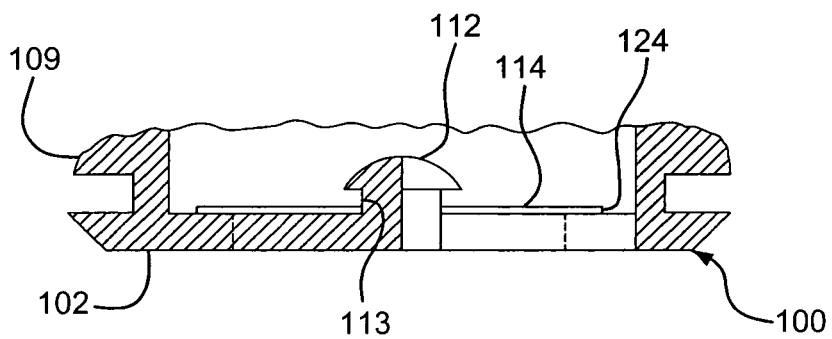
FIG. 11 is an enlarged top plan view in partial cross-section of the modified filter housing shown in FIGS. 5-10 with the valve disc adjacent the frame during inhalation by the patient.

The movement of the valve disc 114 is controlled by the patient's inhalation and exhalation. When air is inhaled, the air forces or drives the valve disc 114 against the frame 102, as seen in FIG. 11. The valve disc 114 is pressed entirely against the cross-shaped surface 104 of the frame 102. Since the space 128 between the perimeter 124 of the valve disc 114 and the outermost part of the apertures 116 is open and not covered by the valve disc 114, a negligible amount of air passes into the mask chamber. This is a fail safe design to prevent the patient from suffocating if the pure oxygen cannot be inhaled through the nose piece of the mask.

Figure 12:
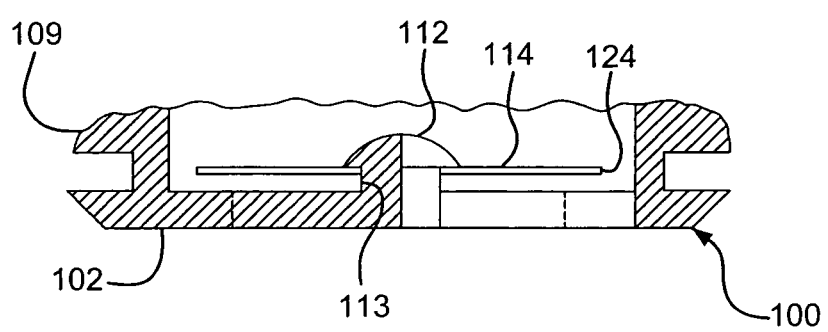
FIG. 12 is an enlarged top plan view in partial cross-section of the modified filter housing shown in FIGS. 5-11 with the valve disc axially displaced outward and adjacent the retainer button during exhalation by the patient.

When air is exhaled, the air forces or drives the valve disc 114 outwardly against the retainer button 112, as seen in FIG. 12. The contents of the air include contaminants from the patient, and it is necessary to prevent the contaminants from reentering the atmosphere and infecting anyone around the patient. The flexibility of the valve disc 114 and movement towards the retainer button 112 allow the air to pass through the apertures 116 and out through the filter housing 40. Thus, the exhaled contaminants will be trapped on the filter media, as described in the first embodiment hereof in FIGS. 1-4.

Figure 13:
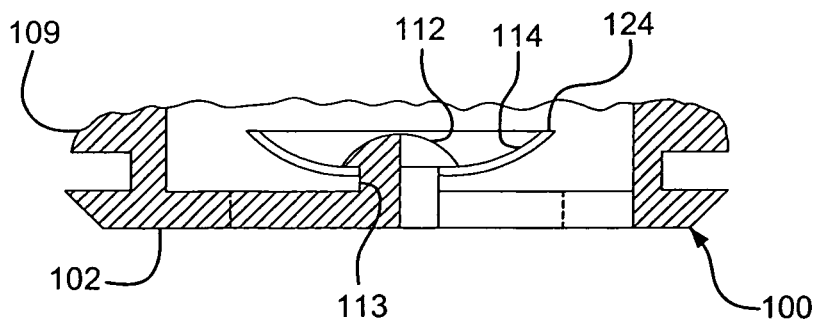
FIG. 13 is an enlarged top plan view in partial cross-section of the modified filter housing shown in FIGS. 5-12 with the valve disc adjacent the retainer button and partially curved outward during exhalation by the patient.

The flexibility of the valve disc 114 permits movement thereof towards and away from the interior of the mask assembly, specifically, the frame 102. With this configuration, air passes around the valve disc 114 in the instance where inhalation through the nasal portion of the oxygen delivery is impaired. When the patient exhales and the expelled air forces the valve disc 114 outwardly towards the retainer button 112, the valve disc 114 can curve or bend, as seen in FIG. 13, such that the perimeter end or rim 124 of the valve disc 114 flexes away from the frame 102 to allow a maximum volume of air away from the interior of the mask chamber.

Assembly and Operation

Assembly and operation of the face mask assembly 10 in accordance with a first exemplary embodiment of the present invention will now be described with reference to FIGS. 1-4.

As best seen in FIGS. 1-4, the filter 52 is first positioned between the filter housing 40 and the cover 60 by snap fitting the two components together. More specifically, the peripheral rim 54 of the filter 52 is secured between the top surface 51 of the flange portion 46 and the inner wall of the cover 60. The substantially V-shaped groove 64 of the cover 60 engages the substantially V-shaped projection 50 of the flange portion 48 to establish a snap-fit connection. Thus, the filter 52 is secured between the filter housing 40 and the cover 60. Lastly, the filter housing 40 is secured to the face piece 20 by pushing the neck portion 42 through the face piece 20 apertures 24 and 26.

Once the mask assembly 10 is constructed and mounted in the desired location on the face piece 22, as hereinbefore described, the apparatus may function by supplying and maintaining a breathable atmosphere within the mask chamber 22. A sufficient supply of fluid available from a pressurized gas source or from the oxygenated air travels through the inhalation adapter 30. The fluid may be mixed with another suitable medium such as aerosolized medicine. For example, aerosolized medication treatment (e.g. Bronchial diluters) and/or oxygen may be provided to patients. The fluid is introduced into the mask chamber 22 via the inhalation aperture 23 in the face piece 22. One or more filter housings 40 allow air to exhaust from the mask chamber 22 through the filter 52 and opening 66 when the patient exhales, thereby maintaining a constant, atmospheric pressure within the mask chamber 22.

The filter 52 secured in the filter housing 40 minimizes or eliminates release of toxins in a patient's exhaled gases and/or surplus aerosolized medication into the ambient air. The device will therefore greatly minimize or eliminate the transfer of bacteria/viruses from an infected patient to healthcare personnel. Interchangeability of the mask assembly 10 is also comparatively easier due to the simple assembly of the filter housing 40 and cover 60. In addition, due to increasing numbers of newly developed aerosol type medications with significant toxicity levels, exposure of healthcare personnel (respiratory therapists, nurses, etc.) administering treatments to patients to free airborne medication mist will be minimized or eliminated. Therefore, the device is of interest to healthcare providers due to the inception of SARS and other infectious respiratory tract diseases.

With respect to the second embodiment of the present invention, operation will be described with reference to FIGS. 5-13.

Figure 10:
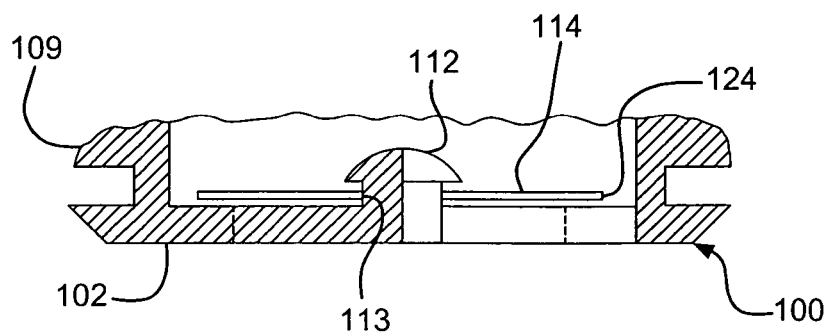
FIG. 10 is an enlarged top plan view in partial cross-section of the modified filter housing shown in FIGS. 5-9 with the valve disc in a stationary, rest position without any air flow.

As best seen in FIG. 10, the flexible valve disc 114 is first positioned substantially midway between the retainer button 112 and the frame 102 and is substantially planar at rest. This is the stationary or rest position when there is no air flowing into or out of the mask assembly. When a patient inhales, the pressure associated with inhalation and the rush of air into the mask assembly causes the valve disc 114 to move away from the retainer button 112 and towards the frame 102. This prevents air from entering the mask assembly through the apertures 116 only adjacent the center 120 of the frame 102.

There is a safety precaution in the instance that the pure oxygen delivered to the patient via the nasal passage fails. The perimeter 124 of the valve disc 114 extends around the apertures 116 and leaves a vent area 128 for the inhalation of air around the valve disc 114. The vent area during inhalation is approximately 0.1 square inch.

Upon exhalation, the valve disc 114 is forced away from the patient and towards the retainer button 112. This movement permits exhaled air to be expelled through a larger surface area than the valve disc 114 allows upon inhalation. Also, the exhaled air includes contaminants from the patient. When this air passes around the valve disc 114, the contaminants are trapped on the filter media, as described in the first embodiment.

While the invention has been shown and described with reference to certain embodiments thereof, it will be understood by those skilled in the art that various changes in form and details may be made therein without departing from the spirit and scope of the invention as defined by the appended claims.

What is claimed is:

1. A face mask assembly for a patient, comprising:
a face piece sized to fit over the patient's nose and mouth, and forming a mask chamber between said face piece and the patient's nose and mouth;
an inhalation adapter coupled to a first opening in said face piece to deliver a fluid to said mask chamber;
at least one filter housing coupled to a second opening of said face piece, said filter housing including a flange portion, an inlet opening communicating with said face piece and defining a passageway connecting said mask chamber to said flange portion;
a filter member coupled to said filter housing;
a retainer button adjacent said face piece and coupled to said filter housing, said retainer button spaced inwardly from said filter member; and
a valve disc coupled to said retainer button adapted to allow gases from said mask chamber to pass through said passageway of said filter housing to said filter member and escape from said passageway to the atmosphere, wherein said valve disc has a dimension less than a dimension of said inlet opening to partially close said inlet opening, and wherein said valve disc opens to allow gases to escape from said face mask and closes to partially close said inlet opening and allow air to enter said face mask.

2. The face mask assembly according to claim 1 wherein said inlet opening includes at least one aperture adjacent said retainer button to allow gases from the atmosphere to pass from said filter member through said aperture into said mask chamber.

3. The face mask assembly according to claim 2 wherein said valve disc has an exterior rim and said aperture extends beyond the exterior rim of said valve disc.

4. The face mask assembly according to claim 1 wherein a plurality of apertures are located in said filter housing adjacent said retainer button wherein at least one of said apertures extends beyond the surface of said valve disc.

5. The face mask assembly according to claim 1 wherein said valve disc is formed of a flexible material.

6. The face mask of claim 1, wherein said valve disc is positioned between said face piece and said filter member.

7. A face mask assembly for a patient, comprising:
a filter housing having a bottom and a frame and adapted to be coupled to a face piece of a face mask, said face piece being sized to fit over a patient's nose and mouth;
a first opening in said frame at a first end of said filter housing;
a filter member coupled to a second end of said filter housing;
a valve disc located adjacent said frame adjacent said first opening, said valve disc being positioned between said filter member and said frame, wherein said valve disc has a dimension less than a dimension of said first opening, said valve disc being movable between a first open position to allow air to exit said face mask assembly when a patient exhales, and a second position to partially close said first opening to limit air entering said face mask assembly when the patient inhales; and
a retainer button coupled to said frame and supporting said valve disc, said retainer button extending toward said filter member.

8. The face mask assembly according to claim 7 wherein said filter housing has a substantially cross-shaped surface disposed adjacent a circular edge of said frame.

9. The face mask assembly according to claim 8 wherein said first opening comprises
a plurality of apertures extending between the cross-shaped surface and said frame.

10. The face mask assembly according to claim 9 wherein openings are formed between an outer edge of said plurality of apertures and the outermost perimeter of said valve disc to define a vent area.

11. The face mask assembly according to claim 9 wherein said plurality of apertures are each shaped substantially as an arrowhead with a point facing a center of said frame.

12. The face mask assembly according to claim 7 wherein an exterior side of said bottom includes a recessed rim adapted to snap-fit into an opening in the face mask assembly.

13. The face mask assembly according to claim 7 wherein said valve disc has a first position adjacent said retainer button having a space between said valve disc and said frame when a patient exhales air.

14. The face mask assembly according to claim 13 wherein said valve disc has a second position adjacent said retainer button having a space between said valve disc and said retainer button when a patient inhales a gas.

15. The face mask assembly according to claim 10 wherein said vent area is about 0.1 square inches.

16. The face mask assembly according to claim 13 wherein the perimeter of said valve disc curves outwardly away from said frame during exhalation of a gas by a patient.

17. The face mask assembly of claim 7, wherein said valve disc is slidably coupled to said retainer button, where said valve disc is spaced from said first opening in said first position and seats against said first opening in said second position.

18. A face mask assembly for a patient, comprising:
a filter housing having a first end and a frame and adapted to be coupled to a face piece of the face mask and sized to fit over a patient's nose and mouth;
a filter member coupled to a second end of said filter housing;
at least one aperture formed in said frame; and
a valve disc coupled to said frame and partially covering said at least one aperture, said valve disc being movable between a first open position with respect to said frame to allow air exhaled by said patient to exit said at least one aperture and said face mask through said filter, and a second position to partially close said at least one aperture to limit incoming air through said filter when the patient inhales.

19. A face mask assembly according to claim 18 wherein said at least one aperture comprises four apertures evenly spaced around said valve disc.

20. A face mask assembly according to claim 18 wherein said frame includes a post, and
said valve disc has a central opening for slidably receiving said post therein.

21. A face mask assembly according to claim 20 wherein said valve disc is formed of flexible material and is slidably mounted on said post to move between said first position where said valve disc is spaced from said frame and said second position where said valve disc seats on said frame.

22. A method of delivering air to a patient, including the steps of
providing a mask assembly having at least one opening adjacent a patient's face,
snapping a filter housing with a bottom into the opening,
coupling a filter housing to a top end of said filter housing,
securing a valve disc to the bottom between a retainer button and a frame of the filter housing, and
distributing oxygen to a patient through the mask assembly and allowing gases to pass into and out of the mask assembly around the valve disc, said frame having an opening and said valve disc having a dimension less than a dimension of said opening, said valve disc being movable between a first open position deflected away from said frame to allow exhaled air to exit through the filter member and a second closed position seated against said frame to limit flow of air to the patient through the filter member when the patient inhales, wherein said valve disc in said first open position allows unobstructed flow of gases from the face mask assembly when the patient exhales and said valve disc in said second closed position partially closes said opening to allow limited air flow into said face mask assembly when the patient inhales.

23. The method according to claim 22, further including the step of
driving the valve disc towards the frame when the patient inhales.

24. The method according to claim 22, further including the step of
driving the valve disc towards the retainer button when the patient exhales.

* * * * *